(12) United States Patent
Wentzel et al.

(10) Patent No.: US 6,666,863 B2
(45) Date of Patent: Dec. 23, 2003

(54) DEVICE AND METHOD FOR PERCUTANEOUS MYOCARDIAL REVASCULARIZATION

(75) Inventors: David E. Wentzel, Issaquah, WA (US); Eric D. Nielson, Bellevue, WA (US)

(73) Assignee: SciMed Life Systems, Inc., Maple Grove, MN (US)

(*) Notice: Subject to any disclaimer, the term of this patent is extended or adjusted under 35 U.S.C. 154(b) by 146 days.

(21) Appl. No.: 09/797,505

(22) Filed: Mar. 1, 2001

(65) Prior Publication Data

US 2002/0123747 A1 Sep. 5, 2002

(51) Int. Cl.[7] .......................... A61B 18/04; A61B 18/18
(52) U.S. Cl. ........................ 606/41; 606/34; 606/42; 607/98; 607/113; 607/119
(58) Field of Search .......................... 606/41, 29, 32, 606/34, 35, 42, 10, 45–50; 607/98, 107–115, 116, 119, 122

(56) References Cited

U.S. PATENT DOCUMENTS

| | | | |
|---|---|---|---|
| 4,658,817 A | 4/1987 | Hardy | 606/19 |
| 5,125,926 A | 6/1992 | Rudko et al. | 606/19 |
| 4,788,975 A | 3/1999 | Shturman et al. | 606/7 |
| 6,369,465 B1 * | 4/2002 | Swanson | 307/112 |
| 6,416,490 B1 * | 7/2002 | Ellis et al. | 604/22 |
| 6,436,095 B1 * | 8/2002 | Ben-Haim et al. | 606/10 |
| 6,461,351 B1 * | 10/2002 | Woodruff et al. | 606/36 |
| 6,468,271 B1 * | 10/2002 | Wentzel et al. | 606/34 |

* cited by examiner

Primary Examiner—Mark Paschall
(74) Attorney, Agent, or Firm—Christensen O'Connor Johnson Kindness PLLC (57) ABSTRACT

Devices and methods for performing percutaneous myocardial revascularization (PMR) are disclosed. A PMR system in accordance with the present invention includes a first electrode disposed proximate the end of a catheter, a second electrode adapted for connection to the body of a patient, and an ablation current source for providing an ablation current. The ablation current source includes a first output coupled to the first electrode and a second output coupled to the second electrode. In a preferred embodiment, the ablation current source has an enabled state in which an ablation current may be passed between the first electrode and the second electrode, and a disabled state in which the passage of an ablation current between the first electrode and the second electrode is prevented. The PMR system also includes an ablation controller coupled to the ablation current source for providing an enable signal to the ablation current source, wherein the enable signal controls whether the ablation current source is in the enabled state or the disabled state. A sensing block for sensing a differential voltage between the first electrode and the second electrode is coupled to the ablation controller. The sensing block includes a first input coupled to the first electrode and a second input coupled to the second electrode.

41 Claims, 11 Drawing Sheets

DEVICE AND METHOD FOR PERCUTANEOUS MYOCARDIAL REVASCULARIZATION

FIELD OF THE INVENTION

The present invention relates generally to devices and methods for promoting blood circulation to the heart muscle. More particularly, the present invention relates to devices and methods for forming holes or channels in the interior walls of a heart chamber as part of a percutaneous myocardial revascularization (PMR) procedure.

BACKGROUND OF THE INVENTION

Assuring that the heart muscle is adequately supplied with oxygen is critical to sustaining the life of a patient. To receive an adequate supply of oxygen, the heart muscle must be well perfused with blood. In a healthy heart, blood perfusion is accomplished with a system of blood vessels and capillaries. However, it is common for the blood vessels to become occluded (blocked) or stenotic (narrowed). A stenosis may be formed by an atheroma which is typically a hard, calcified substance which forms on the walls of a blood vessel.

Historically, individual stenotic lesions have been treated with a number of medical procedures including coronary bypass surgery, angioplasty, and atherectomy. Coronary bypass surgery typically involves utilizing vascular tissue from another part of the patient's body to construct a shunt around the obstructed vessel. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guidewire and a balloon catheter. In these procedures, a balloon catheter is advanced over a guidewire such that the balloon is positioned proximate a restriction in a diseased vessel. The balloon is then inflated and the restriction in the vessel is opened. A third technique which may be used to treat a stenotic lesion is atherectomy. During an atherectomy procedure, the stenotic lesion is mechanically cut or abraded away from the blood vessel wall.

Coronary by-pass, angioplasty, and atherectomy procedures have all been found effective in treating individual stenotic lesions in relatively large blood vessels. However, the heart muscle is perfused with blood through a network of small vessels and capillaries. In some cases, a large number of stenotic lesions may occur in a large number of locations throughout this network of small blood vessels and capillaries. The torturous path and small diameter of these blood vessels limit access to the stenotic lesions. The sheer number and small size of these stenotic lesions make techniques such as cardiovascular by-pass surgery, angioplasty, and atherectomy impractical.

When techniques that treat individual lesion are not practical, a technique known as percutaneous myocardial revascularization (PMR) may be used to improve the oxygenation of the myocardial tissue. A PMR procedure generally involves the creation of holes or channels directly into the myocardium of the heart. PMR was inspired in part by observations that reptilian heart muscles are supplied with oxygen primarily by blood perfusing directly from within heart chambers to the heart muscle. This contrasts with the human heart, which is supplied by coronary vessels receiving blood from the aorta. Positive clinical results have been demonstrated in human patients receiving PMR treatments. These results are believed to be caused because the myocardial tissue is oxygenated by blood flowing through the heart chamber into the newly created holes or channels. In addition, it is believed that new blood vessels may form when the holes and channels begin to heal, which is sometimes referred to as angiogenesis.

A number of methods have been used to create holes and/or channels in the myocardium during percutaneous myocardial revascularization. Methods of cutting include the use of knife-like cutting tools and cutting with light from a LASER. Radio frequency energy have also been used to burn or ablate channels or craters into the myocardial tissue.

SUMMARY OF THE INVENTION

A percutaneous myocardial revascularization (PMR) system in accordance with one embodiment of the present invention includes a first electrode disposed proximate the distal end of a catheter, a second electrode adapted for connection to the body of a patient, and a sensing block coupled to the first electrode and the second electrode. The sensing block is, preferably, adapted to receive electrical signals originating from the heart of the patient and provide an output signal that is related to the cardiac rhythm of the heart. The sensing block output signal may be displayed on a visual output display, and/or may be used to identify if the heart is in a particular wave or portion of the cardiac rhythm.

The PMR system also includes an ablation current source that is coupled to the first electrode and the second electrode for providing an ablation current that burns or ablates channels or craters in the myocardial tissue of the heart when activated. In a preferred embodiment, the ablation current source has an enabled state in which the ablation current passes between the first electrode and the second electrode, and a disabled state in which the ablation current is prevented from passing between the first electrode and the second electrode.

To control the ablation current source, an ablation controller may be provided. The ablation controller may provide an enable signal that controls whether the ablation current source is in the enabled state or the disabled state. The ablation controller preferably receives an output signal from the sensing block. The sensing block may sense a differential voltage between the first electrode and the second electrode, and provide an output signal that is related to the cardiac rhythm of the heart. The ablation controller may analyze the output signal from the sensing block and provide a detect signal when a selected triggering event occurs, such as when the voltage of the output signal crosses a preselected threshold voltage.

In a one embodiment, the detector of the ablation controller may provide a detect signal when the sensor block output signal indicates that the first electrode is touching the wall of the heart. The ablation controller may also provide a detect signal when the heart is in a less vulnerable portion of the cardiac rhythm, such as when the ventricles of the heart are contracting. As such, the ablation controller may be used to help identify when the first electrode is in contact with the wall of the heart, thereby reducing the likelihood that an ablation will be triggered when the first electrode is not in contact with the endocardium of the heart and cause damage to the blood platelets within the heart. The ablation controller may also be used to help synchronize ablation with less vulnerable portions or waves of the cardiac rhythm.

DETAILED DESCRIPTION OF THE INVENTION

The following detailed description should be read with reference to the drawings, in which like elements in different drawings are numbered in like fashion. The drawings which are not necessarily to scale, depict selected embodiments and are not intended to limit the scope of the invention. In some cases, the drawings may be highly diagrammatic in nature. Examples of constructions, materials, dimensions, and manufacturing processes are provided for various elements. Those skilled in the art will recognize that many of the examples provided have suitable alternatives which may be used.

Figure 1:
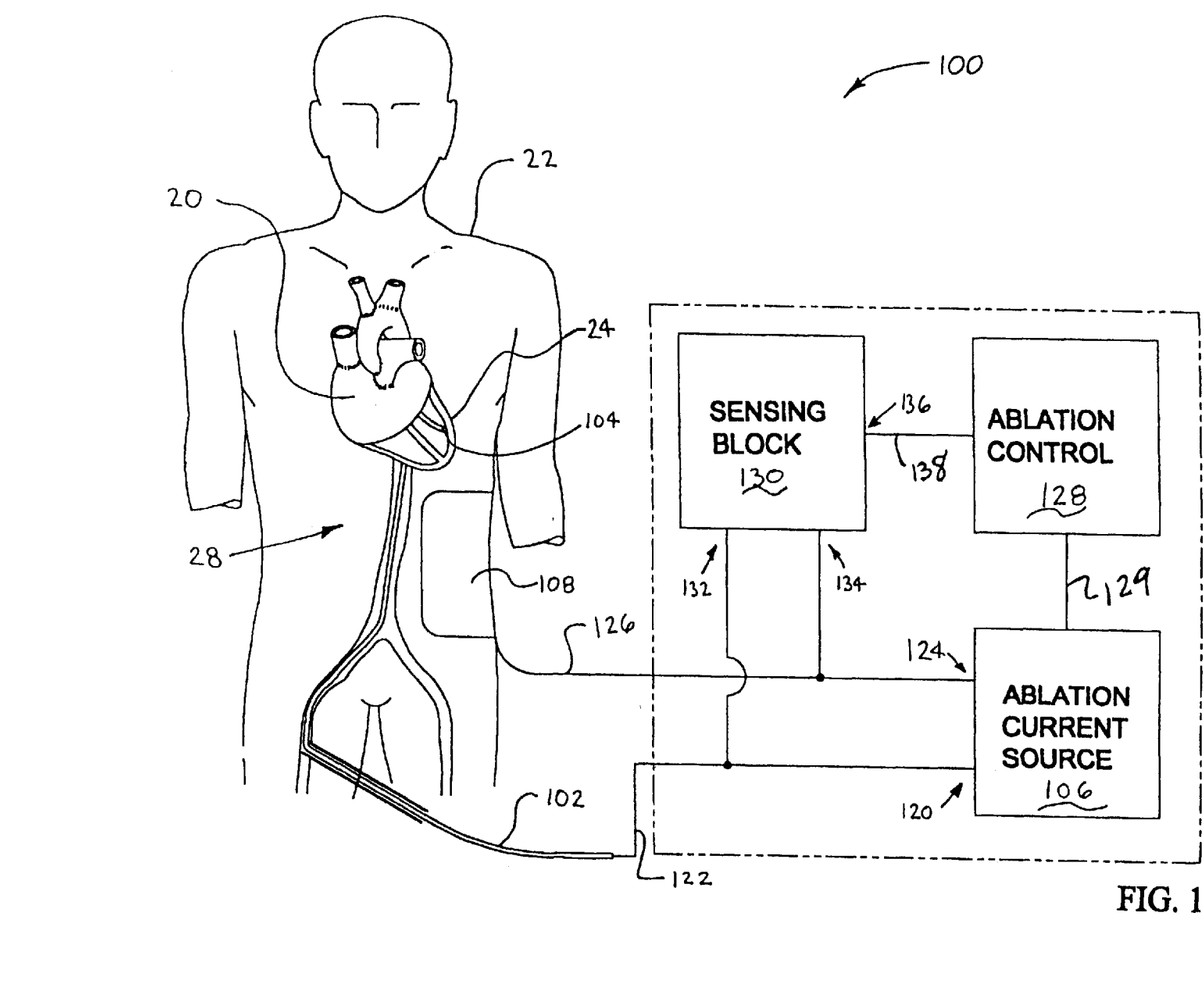
FIG. 1 is a diagrammatic representation of a percutaneous myocardial revascularization system in accordance with an illustrative embodiment of the present invention.

FIG. 1 is a diagrammatic representation of a percutaneous myocardial revascularization (PMR) system 100 in accordance with one embodiment of the present invention. PMR system 100 may be used to perform a percutaneous myocardial revascularization procedure on a heart 20 of a patient 22. System 100 includes a catheter 102 adapted to be inserted into the vasculature system 28 of the patient 22. A first electrode 104 is disposed proximate the distal end of the catheter 102, which is preferably positioned proximate a wall 24 of the heart 20 of the patient 22.

System 100 includes an ablation current source 106 having a first output 120 and a second output 124. First electrode 104 is coupled to the first output 120 of the ablation current source 106 by a first lead 122, which preferably extends along the length of catheter 102. The ablation current source 106 is preferably adapted to produce an ablation signal. The ablation signal may be an alternating current (AC) signal having a frequency in the RF range, and with sufficient energy to ablate tissue proximate the first electrode 104.

System 100 also preferably includes a second electrode 108, which is adapted for connection to the body of a patient. In the embodiment of FIG. 1, second electrode 108 is pictured as a relatively thin pad which conforms to the outside shape of the patient 22. An electrode of this type typically includes a flexible conductive pad, often made from metal foil and/or conductive ink disposed on a polymer substrate. Electrode 108 is preferably adhered to the outside of the patient's 22 body with a conductive adhesive, such as a hyrodgel adhesive.

The second electrode 108 is coupled to the second output 124 of the ablation current source 106 by a second lead 126. In a preferred embodiment, the ablation signal produced by ablation current source 106 passes between the first electrode 104 and the second electrode 108. Because, the tissue contacting area of the second electrode 108 is substantially larger than the tissue contacting area of the first electrode 104, the tissue proximate the first electrode 104 can be ablated, with little or no tissue damage at the second electrode 108.

Having a first electrode disposed as an ablating tool, and a second electrode pad as an exterior contact region is sometimes referred to as a monopolar configuration. In a bi-polar configuration, a second electrode is disposed in close proximity to the first electrode. For example, in the embodiment of FIG. 1 a second electrode may be disposed on an outer surface of the catheter 102 proximate the first electrode 104. It is contemplated that the present invention may be applied to both bipolar or monopolar PMR configurations.

Referring again to FIG. 1, system 100 may also include an ablation controller 128 for providing an enable signal 129 to the ablation current source 106. As described above, the ablation current source 106 is preferably adapted to produce an ablation current between the first electrode 104 and the second electrode 108, when enabled. Thus, ablation current source 104 preferably has an enabled state in which an ablation current passes between the first electrode 104 and the second electrode 108, and a disabled state in which the ablation current is prevented from passing between the first electrode 104 and the second electrode 108. The enable signal 129 of the ablation controller 128 controls whether the ablation current source 106 is in the enabled state or the disabled state.

A sensing block 130 may also be provided for sensing the differential signal between the first electrode 104 and the second electrode 108. A first input 132 of the sensing block 130 is coupled to the first electrode 104, and a second input 134 is coupled to the second electrode 108. Sensing block 130 is preferably adapted to process electrical signals originating from heart 20 of patient 22. Sensing block 130 includes a sensing block output 136, which is coupled to ablation controller 128.

Figure 2:
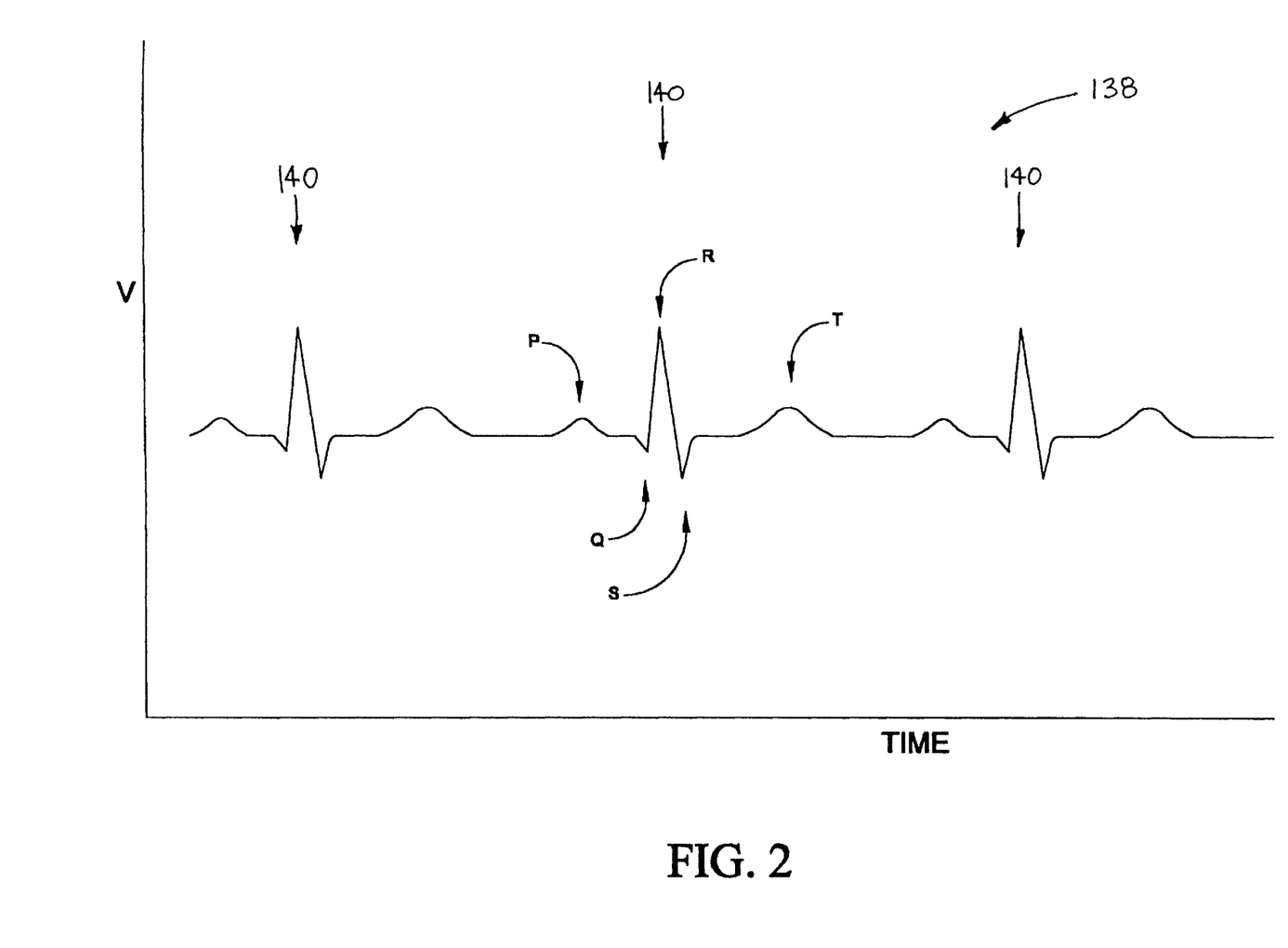
FIG. 2 is a timing diagram of an output signal from a sensing block of a percutaneous myocardial revascularization system in accordance with an illustrative embodiment of the present invention.

FIG. 2 is a diagrammatic representation of an exemplary sensing block output signal 138 produced by sensing block 130. Sensing block output signal 138 preferably includes a plurality of heartbeat waveforms 140. Each heartbeat waveform 140 includes five component waves designated "P", "Q", "R", "S" and "T". The first component wave occurring in each heartbeat waveform 140 is the P-wave which electronically represents an atrial beat associated with atrial depolarization.

The Q, S, and R component waves are electrical signals indicative of the depolarization and electrical actuation of the ventricles of the heart. The R-wave is the electrical activity in the heart that stimulates a ventricular contraction. In FIG. 2, the R-wave appears as a generally triangular pulse. The T-wave follows the R wave by about 0.3 seconds. The T-wave is an electrical signal indicative of the repolarization of the ventricles.

A number of factors may disrupt the normal heart rhythym causing a cardiac arrhythmia. Examples of cardiac arrhythmia's include tachycardia and ventricular fibrillation. Ventricular fibrillation is a rapid, and disorganized firing of muscle fibers within the ventricular myocardium. During ventricular fibrillation, the ventricles do not contract in an organized manner, no blood is pumped, and blood pressure falls to zero. Patient death may occur within 4 minutes from the onset of ventricular fibrillation.

One factor that may initiate a cardiac arrhythmia is electric current traveling through or proximate the heart. The cardiac cycle includes more vulnerable portions during which the heart is more susceptible to cardiac arrhythmia's, and less vulnerable portions during which the heart is less susceptible to cardiac arrhythmia. Examples of more vulnerable portions of the cardiac rhythm include the T-wave portion shown in FIG. 2. Examples of less vulnerable portions of the cardiac rhythm include the R-wave portion. In a preferred embodiment of system 100, the ablation enable signal 129 supplied by ablation controller 128 is asserted during a less vulnerable portion of the cardiac rhythm and ends prior to the beginning of a more vulnerable portion of the cardiac rhythm.

Figure 3:
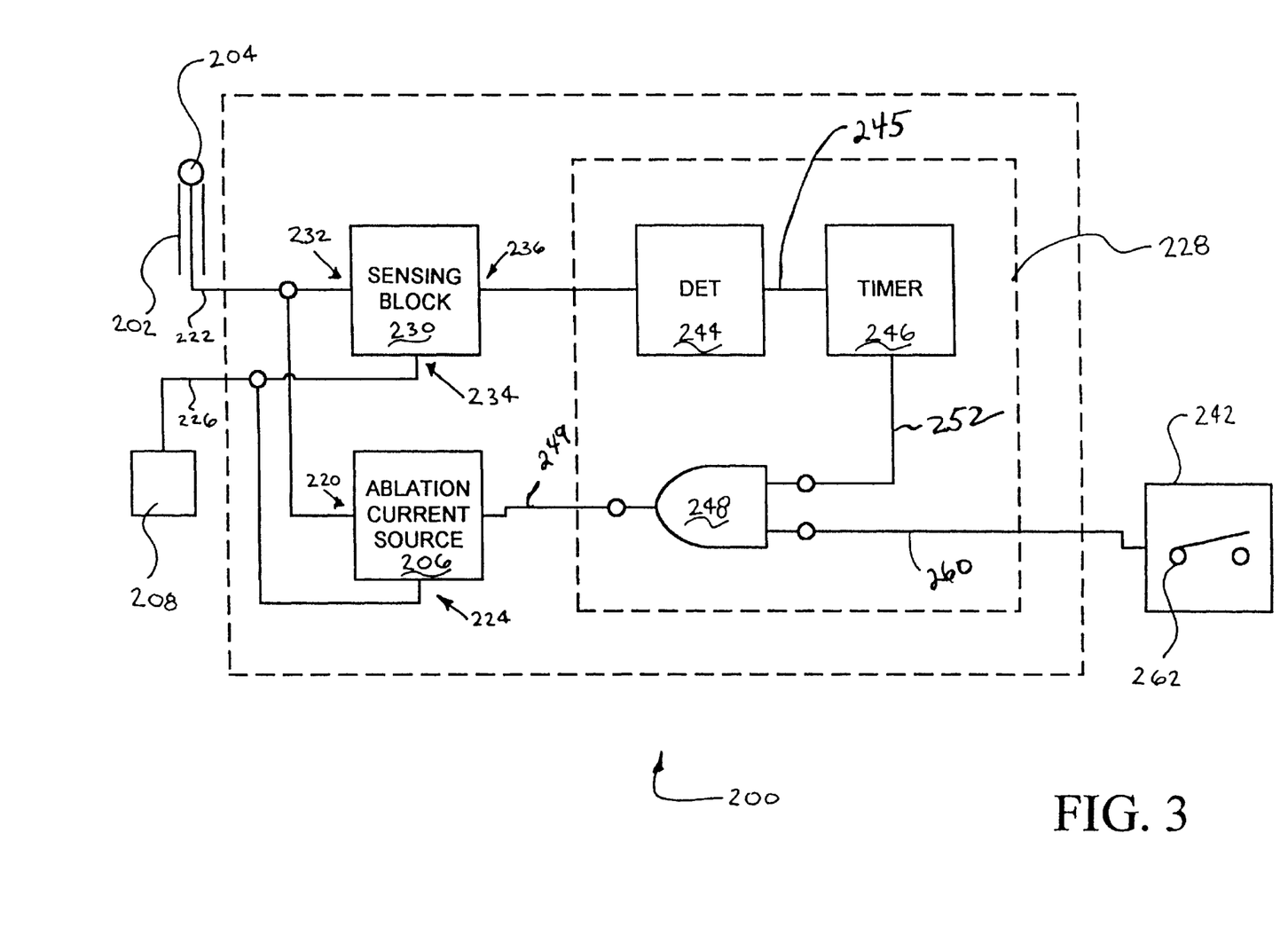
FIG. 3 is a block diagram of a percutaneous myocardial revascularization system similar to that shown in FIG. 1, detailing the ablation control block.

FIG. 3 is a block diagram of a percutaneous myocardial revascularization (PMR) system 200 similar to that shown in FIG. 1, detailing the ablation control block. System 200 includes a user interface 242, an ablation controller 228, a sensing block 230 and an ablation current source 206. Ablation controller 228 includes a detector 244, a timer 246, and an AND operator 248. Detector 244 has a detector input which is coupled to a sensing block output 236 of sensing block 230. Like above, sensing block 230 has a first input 232 coupled to a first electrode 204 and a second input 234 coupled to a second electrode 208. First electrode 204 is preferably disposed proximate the distal end of a catheter 202, and second electrode 208 is preferably disposed on the outside skin of the patient. Sensing block 230 preferably provides a sensing block output signal 250 which is illustrated in FIG. 4.

Figure 4:
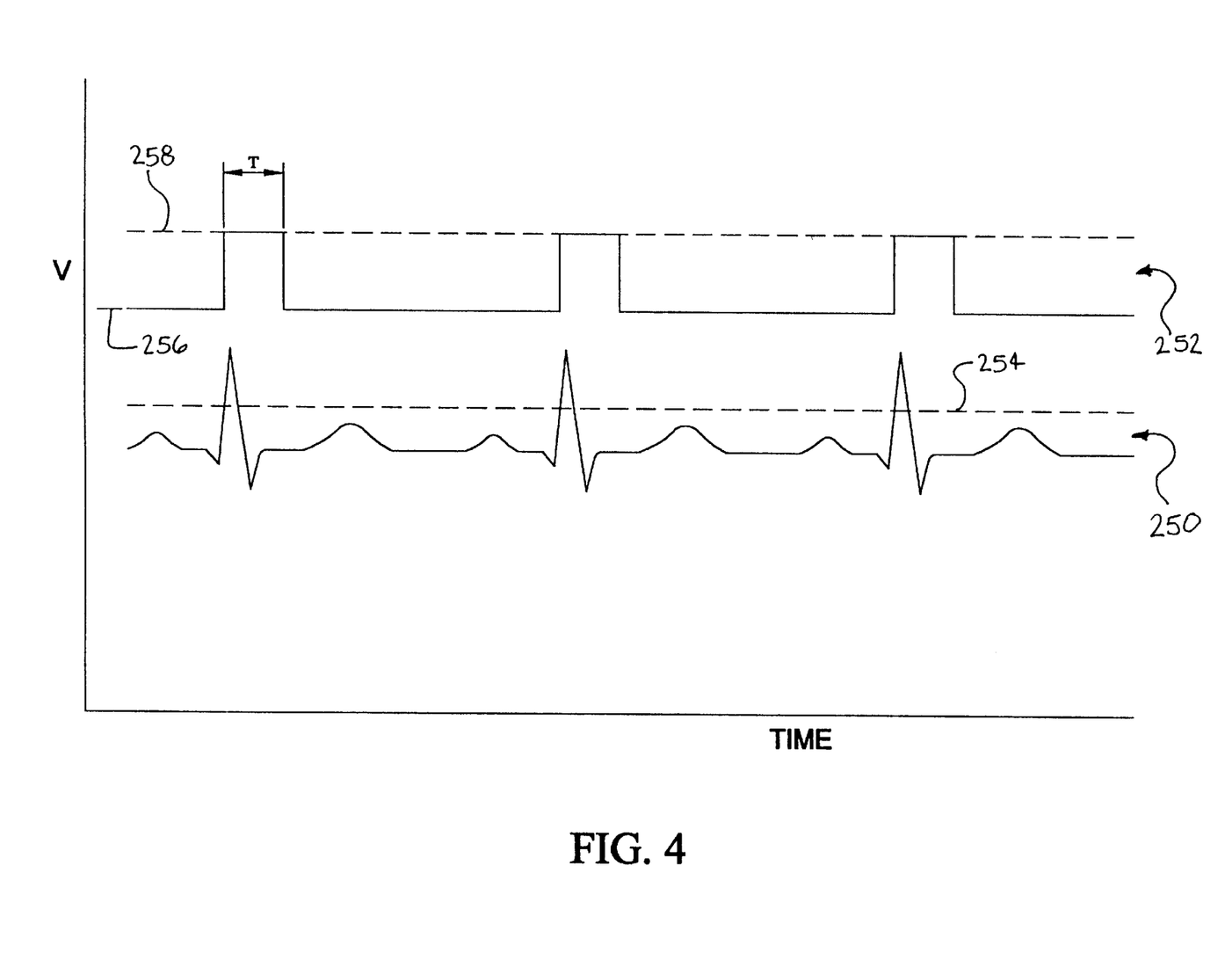
FIG. 4 is a timing diagram showing a sensing block signal and a timer signal in accordance with an illustrative embodiment of the present invention.

FIG. 4 is a timing diagram illustrating the sensing block output signal 250 provided by sensing block 230, and a timer signal 252 provided by timer 246. The sensing block 230 provides sensing block output signal 250 to the detector 244 of ablation controller 228. Detector 244 is adapted to provide a detect signal 245 to timer 246 when a triggering event occurs, such as when the sensing block output signal 250 crosses a predefined threshold voltage 254.

Timer 246 provides a timer signal 252 to the AND operator 248 of ablation controller 228. When timer 246 receives a detect signal from detector 244, the timer signal 252 switches from a low logic state 256 to a high logic state 258. The timer 246 preferably has a pre-selected or programmable countdown time T. As shown in FIG. 4, timer signal 252 remains in the high logic state 258 for time T before returning to the low logic state 256. When both timer signal 252 and the user supplied input signal 260 are high, the AND operator 248 enables the ablation current source 206.

Preferably, threshold voltage 254 is selected to correspond to a sensing block output signal voltage that occurs when first electrode 204 touches the wall of the heart, and/or when the heart is in a less vulnerable portion of the cardiac rhythm, such as when the ventricles of the heart are contracting. As such, ablation controller 228 may be used to prevent the ablation current from being activated by the user switch 262 when; 1) the first electrode 204 is not contacting the wall of the heart; 2) the heart is in a more vulnerable portion of the cardiac rhythm; or 3) when the user switch 262 is not activated. Thus, when PMR system 200 is utilized in a PMR procedure, a physician may depress switch 262 to indicate that an ablation is desired, but the ablation current is only activated when the timer 246 is high indicating that electrode 204 is in contact with the wall of the heart and/or the heart is in a less vulnerable portion of the cardiac rhythm.

Time T is preferably selected so that timer signal 252 reverts back to low logic state 256 before the beginning of a vulnerable portion of the cardiac rhythm, thereby causing the ablation current to cease before the a vulnerable portion of the cardiac rhythm begins. In a particularly preferred embodiment, time T is selected so that timer signal 252 returns to the low logic state 256 before the beginning of the T-wave portion shown in FIG. 2. It is believed that the cardiac rhythm is particularly sensitive to disruption during the T-wave portion of the cardiac rhythm.

Preferably, time T has a duration between about 0.01 seconds and about 1.00 second. More preferably, time T has a duration between about 0.06 seconds and about 0.60 seconds. Even more preferably, time T has a duration between about 0.10 seconds and about 0.30 seconds.

The threshold voltage 254 preferably has a value between about 2 mV and 2000 mV. More preferably, threshold voltage 254 has a value between about 500 mV and about 1500 mV. Even more preferably, threshold voltage 254 has a value between about 900 mV and about 1100 mV.

Returning to FIG. 3, it may be appreciated that system 200 may include an ablation current source 206 having a first output 220 and a second output 224. The first output 220 of the ablation current source 206 is coupled to the first electrode 204 by a first lead 222. Likewise, the second output 224 of the ablation current source 206 is coupled to the second electrode 208 by a second lead 226. In a preferred embodiment, ablation current source 204 has an enabled state in which an ablation signal is passed between the first electrode 204 and the second electrode 208, and a disabled state in which the passage of an ablation signal between the first electrode 204 and the second electrode 208 is prevented. Enable signal 249 provided by the AND operator 248 of the ablation controller 228 controls whether the ablation current source 206 is in the enabled state or the disabled state.

As indicated above, system 200 may include a user interface 242. User interface 242 may be one of various controls without deviating from the spirit and scope of the present invention. Examples of controls which may be suitable in some applications include a switch (e.g., a foot switch), a keypad, a keyboard, a mouse, a track ball, a joy stick, or any other type of triggering or selecting mechanism.

Figure 5:
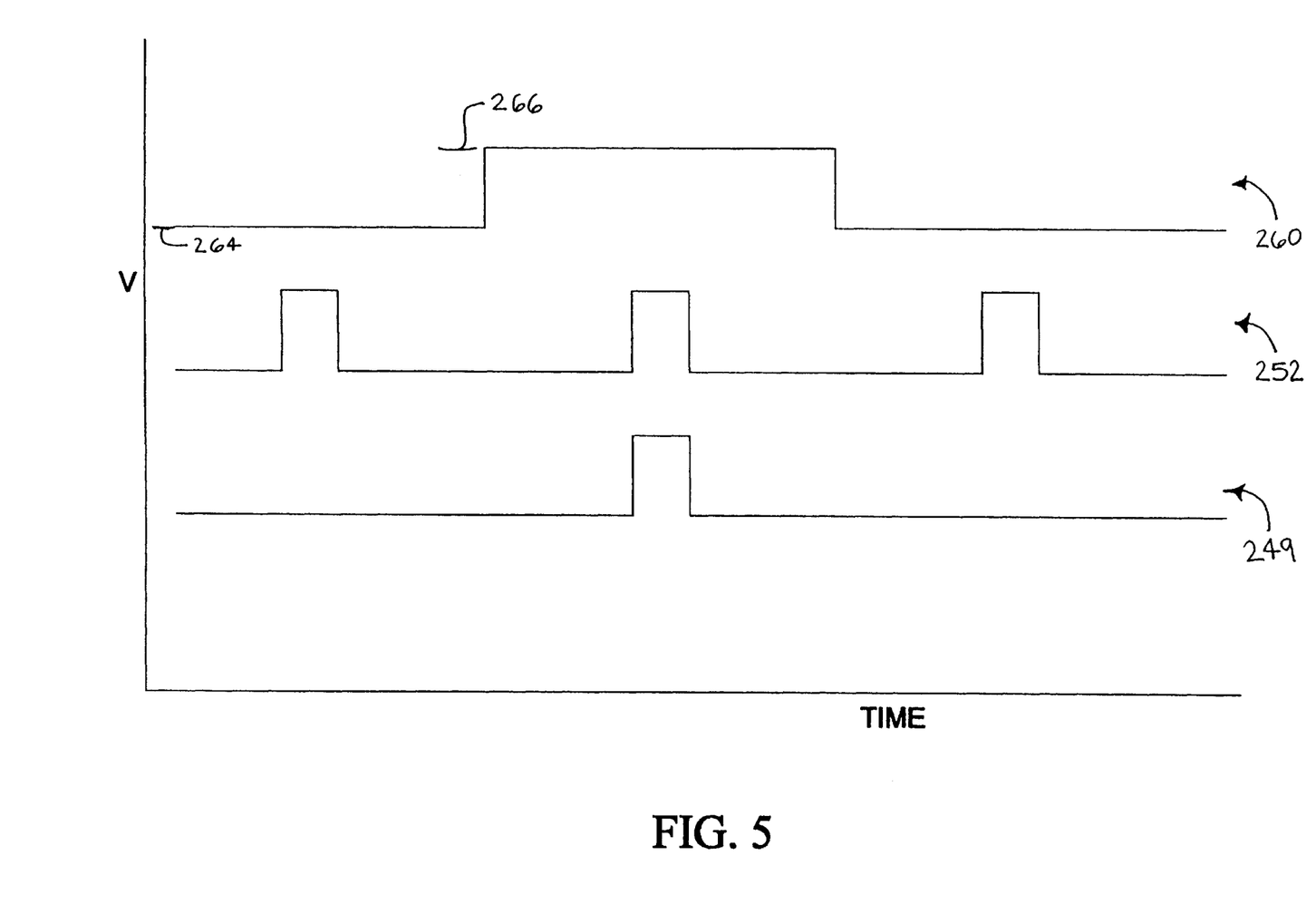
FIG. 5 is a timing diagram showing a user signal, a timer signal, and an enable signal in accordance with an illustrative embodiment of the present invention.

FIG. 5 is a timing diagram illustrating a user signal 260 provided by user interface 242, the timer signal 252 provided by timer 246, and the enable signal 249 provided by AND operator 248. When timer signal 252 and user signal 260 are both in a high logic state, the enable signal 249 also goes to a high logic state (enable). Likewise, when the timer signal 252 or the user signal 260 are in the low logic state, the enable signal 249 is forced to a low logic state (disable).

Figure 6:
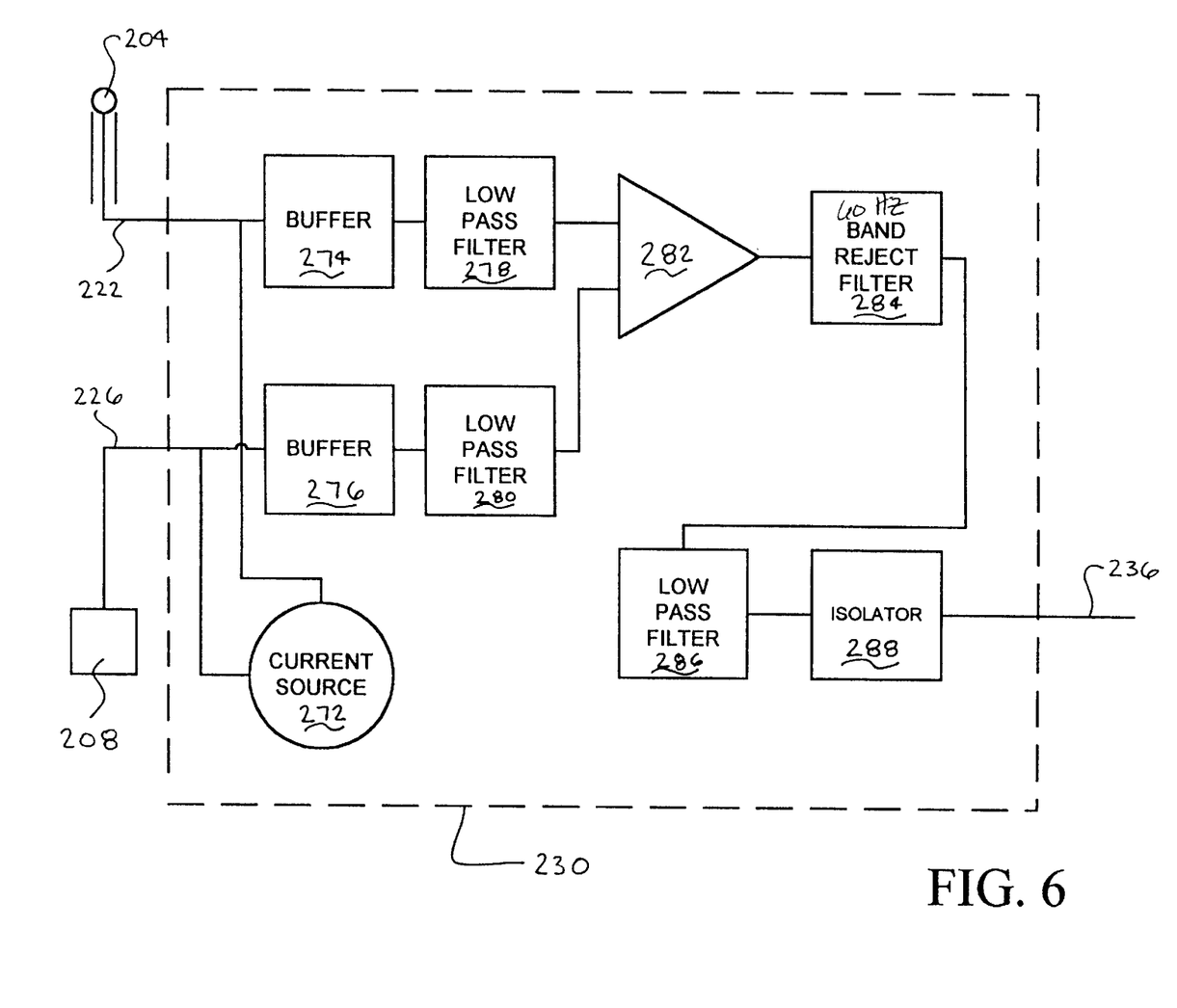
FIG. 6 is a block diagram of an illustrative sensing block in accordance with the present invention.

FIG. 6 is a block diagram of an illustrative sensing block 230 of FIGS. 1 and 3. The illustrative sensing block 230 includes a sense current source 272 for providing a sense current to the first electrode 204 and the second electrode 208. Sensing block 230 also includes a first buffer 274 and a second buffer 276. The input of the first buffer 274 is coupled to the first electrode 204 via the first lead 222, and the input of the second buffer 276 is coupled to the second electrode 208 via the second lead 226. The first buffer 274 and the second buffer 276 preferably have a high input impedance, such as greater than about 1 M$\Omega$.

The outputs of the first buffer 274 and the second buffer 276 are coupled to a first low pass filter 278 and a second low pass filter 280, respectively. Preferably, the first low pass filter 278 and the second low pass filter 280 reject signals having a frequency greater than about 500 kHz. More preferably, the first low pass filter 278 and the second low pass filter 280 reject signals having a frequency greater than about 2 kHz. Even more preferably, the first low pass filter 278 and the second low pass filter 280 reject signals having a frequency greater than about 20 Hz.

Rather than providing separate elements, it is contemplated that first buffer 274 and first low pass filter 278 may be replaced with an active filter. Likewise, the second buffer 276 and second low pass filter 280 may be replaced with a second active filter. Active filters are common, and often include an operational amplifier coupled to a network of passive elements adapted to achieve the desired filter characteristics. First low pass filter 278 and second low pass filter 280 preferably reject all noise signals above the desired cardiac rhythm signal, which is commonly less than 10 Hz, and more commonly less than 4 Hz. The outputs of the first low pass filter 278 and the second low pass filter 280 are coupled to the inputs of a differential amplifier 282. A differential amplifier 282 rejects all common mode noise.

The output of differential amplifier 282 is coupled to a band reject filter 284. Band reject filter 284 may be used to reject electrical noise of a particular frequency, such as 60 Hertz. In the United States, the electrical power grid is 120 Volts AC with a frequency 60 Hertz. In this environment, an embodiment of band reject filter 284 which is adapted to reject signals having a frequency of about 60 Hertz may be desirable. By way of a second example, in Europe, the electrical power grid is 220 Volts AC with a frequency of 50 Hertz. In this environment, an embodiment of band reject filter 284 which is adapted to reject signals having a frequency of about 50 Hertz may be desirable. Embodiments of band reject filter 284 have also been envisioned, in which band reject filter 284 includes a plurality of filtering circuits. For example, one filtering circuit may reject signals having frequencies of about 50 Hertz and a second filtering circuit may reject signals having frequencies of about 60 Hertz.

The output of band reject filter 284 is coupled to another low pass filter 286. The low pass filter 286 is preferably adapted to reject any signal having a frequency greater than the frequency of the electrical signal originating from the heart of a patient. In a preferred embodiment, low pass filter 286 is adapted to reject any signal having a frequency greater than about 20.0 Hertz. In a particularly preferred embodiment, low pass filter 286 is adapted to reject any signal having a frequency greater than about 4.0 Hertz.

Like the first low pass filter 278 and the second low pass filter 280, the low pass filter 286 may be a passive filter, or an active filter that is adapted to amplify the desired frequency components while rejecting all other undesireable frequencies. The output of the low pass filter 286 is coupled to an isolator 288, such as an optical isolator. Optical isolators are commercially available from various companies including Toshiba and Omron Electronics.

Figure 7:
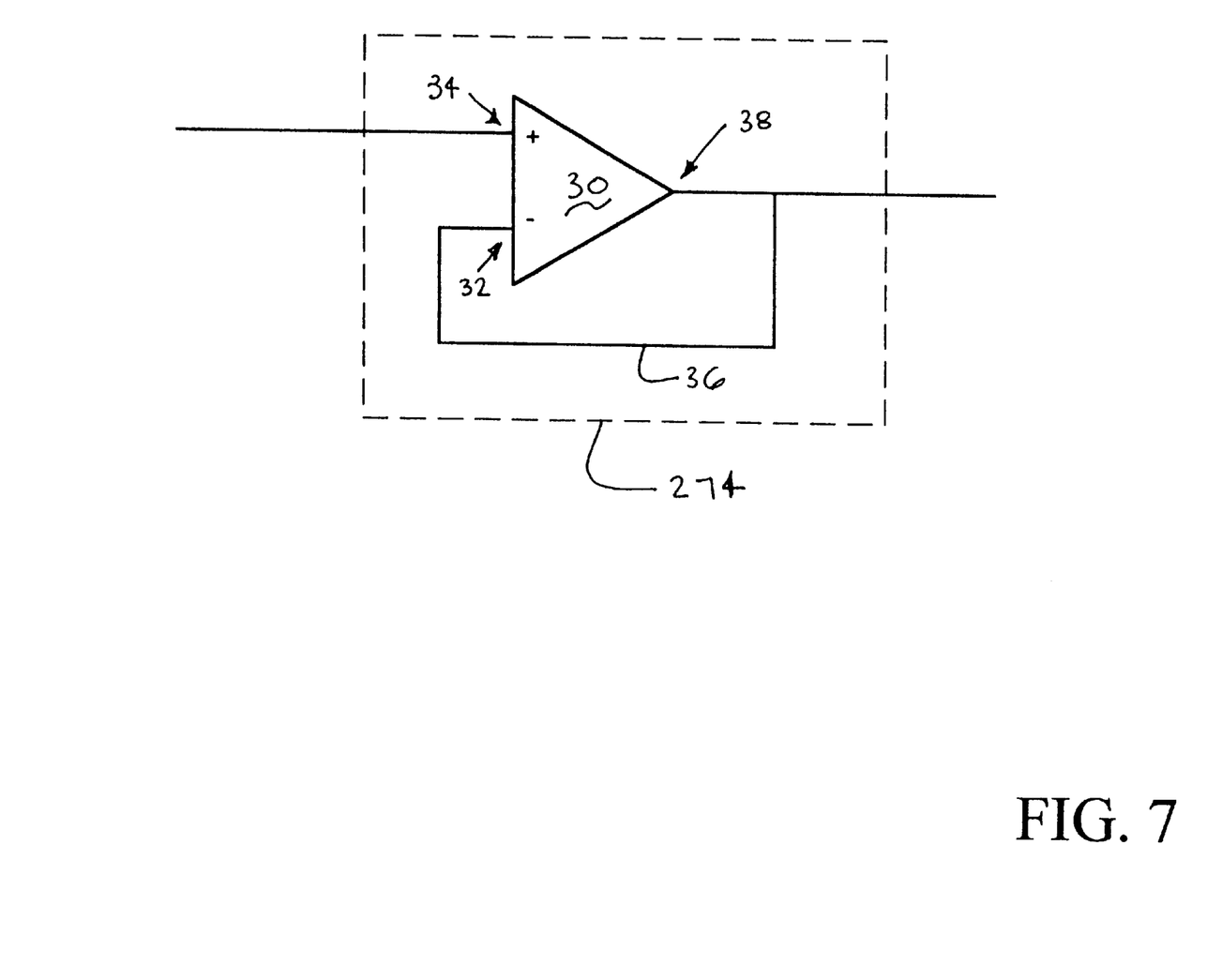
FIG. 7 is a schematic diagram of an illustrative buffer of FIG. 6.

FIG. 7 is a schematic diagram of an illustrative buffer 374 that may be used as buffer 274 of FIG. 6. In the embodiment of FIG. 7, buffer 374 includes an operational amplifier 30 having a non-inverting input 34, an inverting input 32, and an output 38. The output 38 of the operational amplifier 30 is coupled to the inverting input 32, thereby forming a non-inverting buffer circuit.

Figure 8:
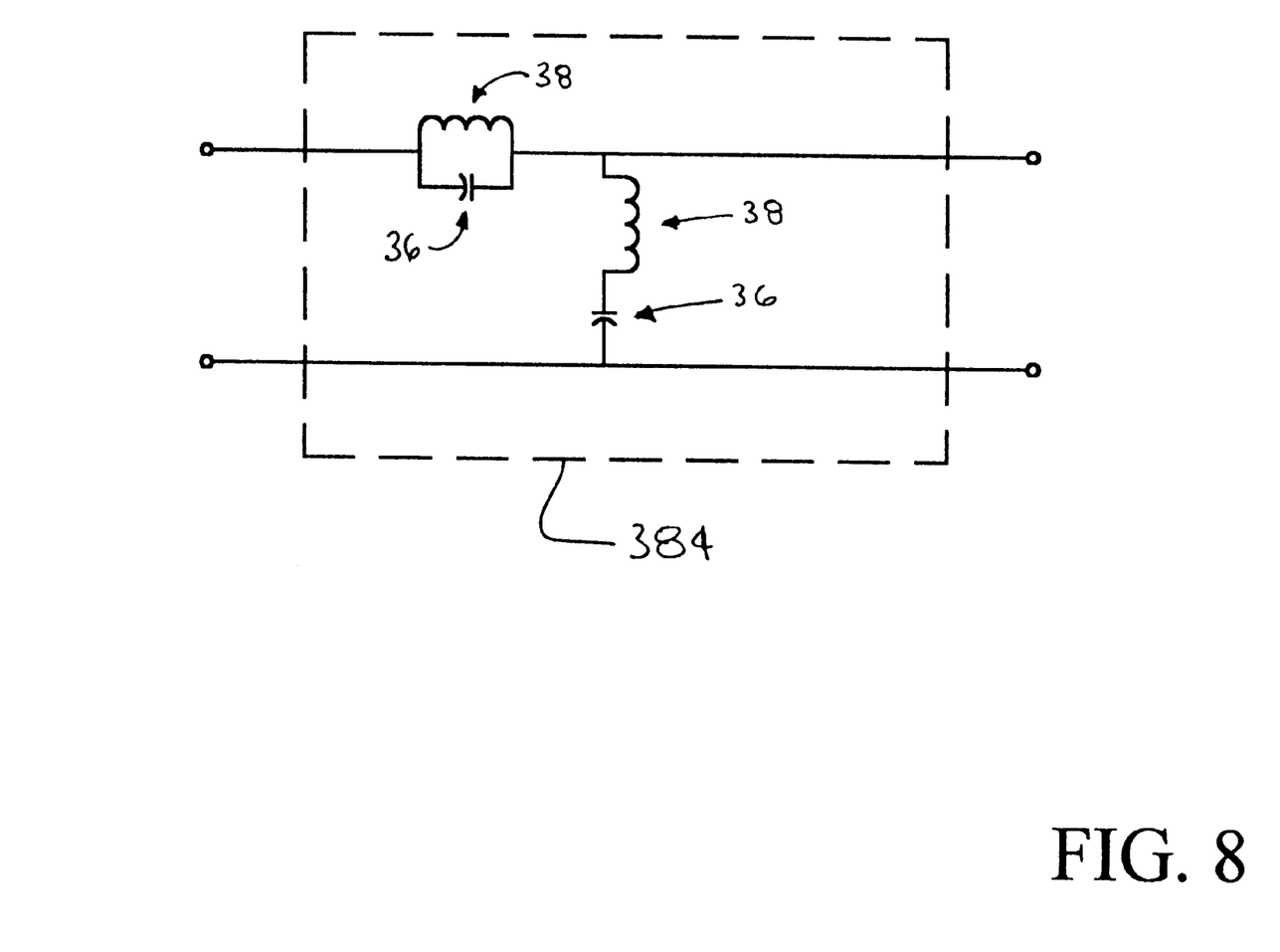
FIG. 8 is a schematic diagram of an illustrative band reject filter of FIG. 6.

FIG. 8 is a schematic diagram of an illustrative embodiment of a band reject filter 384 which may be utilized as band reject filter 284 of FIG. 6. Band reject filter 384 comprises a plurality of capacitors 36 and a plurality of inductors 38. In the embodiment of FIG. 8, capacitors 36 and inductors 38 are coupled together in an L-section configuration.

Figure 9:
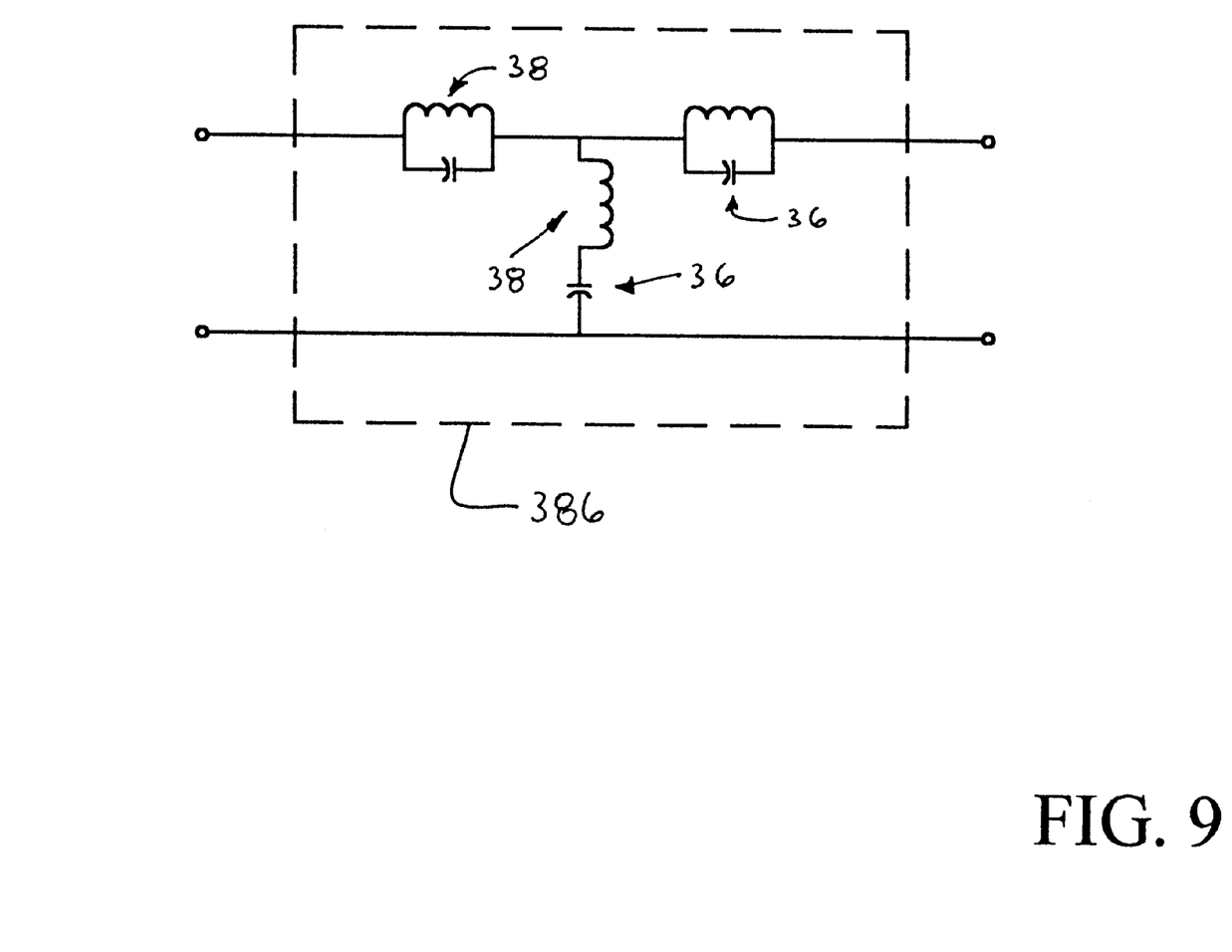
FIG. 9 is a schematic diagram of an alternate embodiment of the band reject filter of FIG. 6.

FIG. 9 is a schematic diagram of an illustrative embodiment of a band reject filter 386 which may be utilized as band reject filter 284 of FIG. 6. Band reject filter 386 comprises a plurality of capacitors 36 and a plurality of inductors 38. In the embodiment of FIG. 8, capacitors 36 and inductors 38 are coupled together in a T-section configuration.

Figure 10:
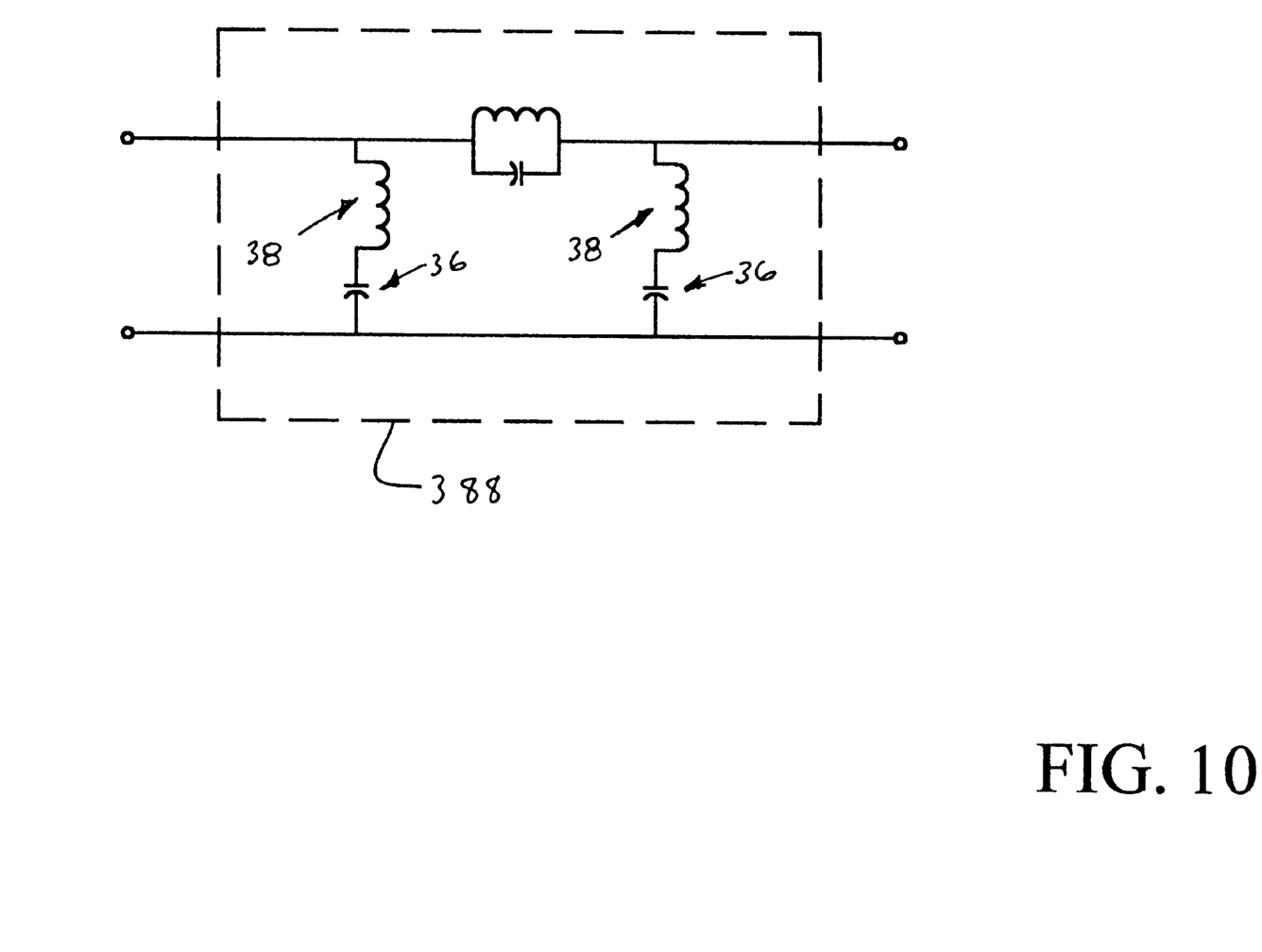
FIG. 10 is a schematic diagram of yet another embodiment of the band reject filter of FIG. 6.

FIG. 10 is a schematic diagram of an illustrative embodiment of a band reject filter 388 which may be utilized as band reject filter 284 of FIG. 6. Band reject filter 388 comprises a plurality of capacitors 36 and a plurality of inductors 38. In the embodiment of FIG. 8, capacitors 36 and inductors 38 are coupled together in a π-section configuration.

Figure 11:
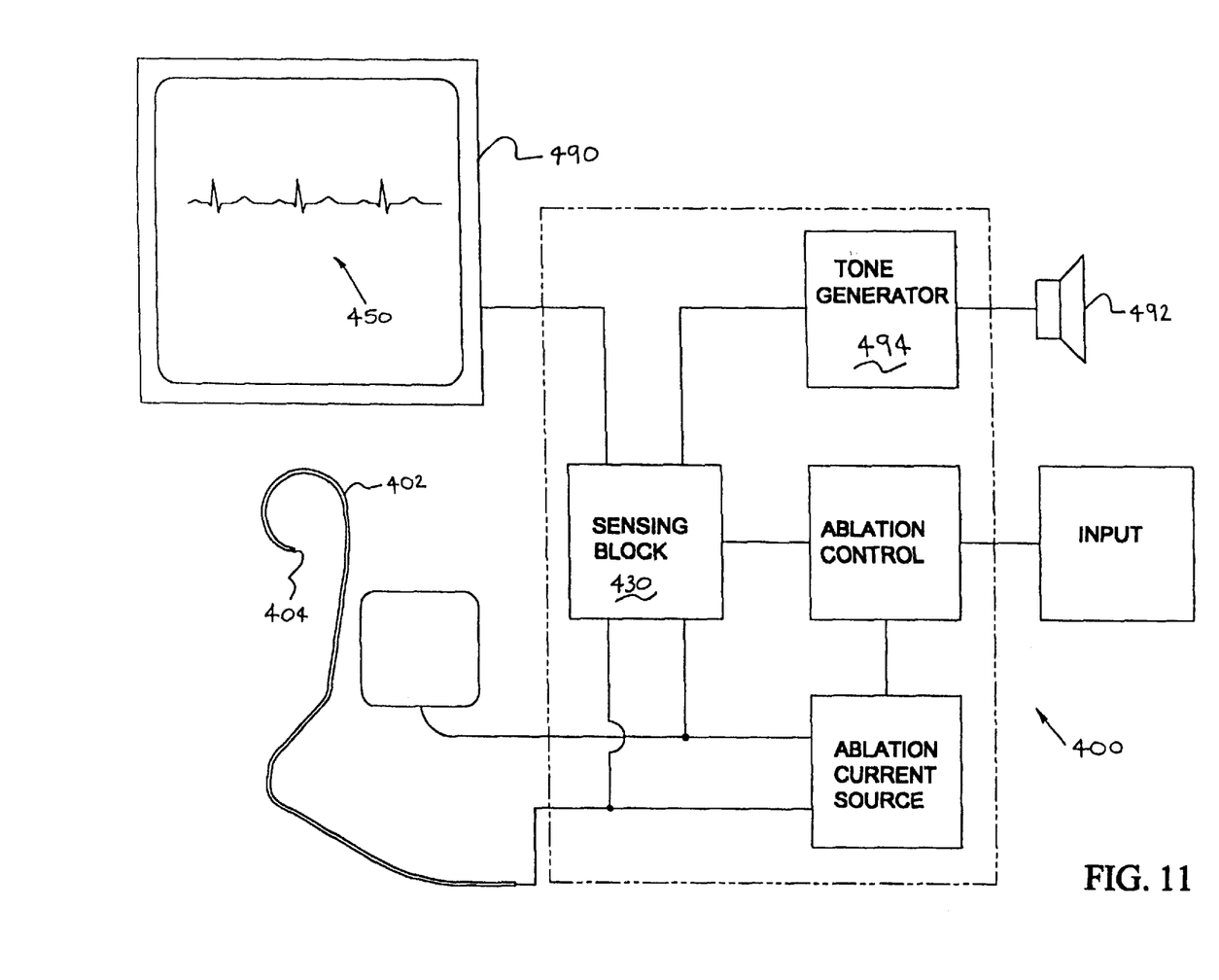
FIG. 11 is a diagrammatic representation of a percutaneous myocardial revascularization system in accordance with another illustrative embodiment of the present invention.

FIG. 11 is a diagrammatic representation of an additional embodiment of a PMR system 400 in accordance with the present invention. PMR system 400 includes a visual output device 490 and an audio output device 492. Visual output device 490 may include various displays without deviating from the spirit and scope of the present invention. Examples of displays include cathode ray tubes, liquid crystal displays (LCD's), and the like. Visual output device 490 is coupled to a sensing block 430. The sensing block 430 provides a sensing block signal 450, which is then displayed on visual output device 490. It is contemplated that additional information may also be displayed on visual display device, if desired.

Audio output device 492 may be an audio speaker, a piezoelectric transducer, or any other mechanism for making sound. Audio output device 492 is coupled to a sound or tone generator 494. Sound or tone generator 494 is coupled to sensing block 430. In a preferred embodiment, sound or tone generator 494 modulates the tone produced by audio output device 492 to reflect the level of the sensing block signal 450. Listening to this tone may allow a user to develop a feel for the proximity and condition of the tissue proximate the first electrode 404. An advantage of this system is that the user can obtain audible information while looking at something other than PMR system 400, for example, when the user needs to be looking at the patient.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A system for performing percutaneous myocardial revascularization on a patient's heart, comprising:
   a first electrode that is to be positioned adjacent to a heart wall;
   a second electrode that collects an ablation current transmitted from the first electrode;
   an ablation current source for providing an ablation current;
   the ablation current source having a first output coupled to the first electrode and a second output coupled to the second electrode;
   the ablation current source having an enabled state in which an ablation current is passed between the first electrode and the second electrode, and a disabled state in which the passage of an ablation current is prevented from passing between the first electrode and the second electrode;

sensing means coupled to the first electrode and the second electrode for sensing a physiological signal induced between the first electrode and the second electrode; and an ablation controller coupled to the ablation current source for providing an enable signal to the ablation current source, such that the ablation current source is only enabled during a less vulnerable portion of the heart's cardiac cycle.

2. The system of claim 1, wherein the sensing means provides an output signal that is indicative of the cardiac rhythm of the patient.

3. The system of claim 2, wherein the ablation controller receives the output signal of the sensing means and identifies a less vulnerable portion of the cardiac rhythm.

4. The system of claim 2, wherein the ablation controller receives the output signal of the sensing means and identifies a contracting portion of the cardiac rhythm.

5. The system of claim 2, wherein the ablation controller receives the output signal of the sensing means and identifies an R-wave portion of the cardiac rhythm.

6. The system of claim 1, wherein the sensing means includes a low pass filter adapted to reject frequencies above a range of expected frequencies that are indicative of the cardiac rhythm of the patient.

7. The system of claim 6, wherein the low pass filter is adapted to reject frequencies above about 4 Hz.

8. The system of claim 1, wherein the ablation controller includes a timer for providing a timer signal.

9. The system of claim 2, wherein the timer has a preset time.

10. The system of claim 9, wherein the preset time corresponds to the length of a less vulnerable portion of the cardiac rhythm.

11. The system of claim 9, wherein the preset time corresponds to the elapsed time between a triggering event and the beginning of a more vulnerable portion of the cardiac rhythm.

12. A system for performing percutaneous myocardial revascularization of a heart muscle, comprising:

a first electrode disposed proximate a distal end of a catheter;

a second electrode adapted for connection to the body of a patient;

an ablation current source for providing an ablation current;

the ablation current source having a first output coupled to the first electrode and a second output coupled to the second electrode;

an ablation controller coupled to the ablation current source for providing an enable signal to the ablation current source;

sensing means coupled to the first electrode and the second electrode for sensing a physiological signal induced between the first electrode and the second electrode and for providing an output signal to the ablation controller;

wherein the ablation controller does not provide the enable signal to the ablation current source during a vulnerable portion of the heart muscle's cardiac rhythm.

13. The system of claim 12, wherein the sensing means provides an output signal that is indicative of the cardiac rhythm of the patient.

14. The system of claim 13, wherein the ablation controller receives the output signal of the sensing means and identifies a less vulnerable portion of the cardiac rhythm.

15. The system of claim 13, wherein the ablation controller receives the output signal of the sensing means and identifies a contracting portion of the cardiac rhythm.

16. The system of claim 13, wherein the ablation controller receives the output signal of the sensing means and identifies an R-wave portion of the cardiac rhythm.

17. The system of claim 1, wherein the sensing means includes a low pass filter adapted to reject frequencies above a range of expected frequencies that are indicative of the cardiac rhythm of the patient.

18. The system of claim 17, wherein the low pass filter is adapted to reject frequencies above about 4 Hz.

19. The system of claim 12, wherein the ablation controller includes a timer for providing a timer signal.

20. The system of claim 19, wherein the timer has a preset time.

21. The system of claim 20, wherein the preset time corresponds to the length of a less vulnerable portion of the cardiac rhythm.

22. The system of claim 20, wherein the preset time corresponds to the elapsed time between a triggering event and the beginning of a more vulnerable portion of the cardiac rhythm.

23. A system for performing percutaneous myocardial revascularization of a patient's heart muscle, comprising:

a first electrode that delivers an ablation current to the patient's heart muscle;

a second electrode that collects the ablation current from the first electrode;

an ablation current source for providing an ablation current;

the ablation current source having a first output coupled to the first electrode and a second output coupled to the second electrode;

the ablation current source having an enabled state in which an ablation current is passed between the first electrode and the second electrode, and a disabled state in which the passage of an ablation current is prevented from passing between the first electrode and the second electrode; and an ablation controller coupled to the ablation current source for providing an enable signal to the ablation current source that controls whether the ablation current source is in the enabled state or the disabled state;

sensing means coupled to the first electrode and the second electrode for sensing a signal indicative of the heart muscle's rhythm cycle that is induced between the first electrode and the second electrode, the sensing means having an output coupled to the ablation controller, wherein the ablation controller operates to enable the ablation current source during a less vulnerable portion of the heart muscle's rhythm cycle.

24. The system of claim 23, wherein the ablation controller receives the output signal of the sensing means and identifies a less vulnerable portion of the cardiac rhythm.

25. The system of claim 23, wherein the ablation controller receives the output signal of the sensing means and identifies a contracting portion of the cardiac rhythm.

26. The system of claim 23, wherein the ablation controller receives the output signal of the sensing means and identifies an R-wave portion of the cardiac rhythm.

27. The system of claim 23, wherein the sensing means includes a low pass filter adapted to reject frequencies above a range of expected frequencies that are indicative of the cardiac rhythm of the patient.

28. The system of claim 27, wherein the low pass filter is adapted to reject frequencies greater than about 4 Hertz.

29. The system of claim 23, wherein the ablation controller includes a timer for providing a timer signal.

30. The system of claim 29, wherein the timer has a preset time.

31. The system of claim 30, wherein the preset time corresponds to the length of a less vulnerable portion of the cardiac rhythm.

32. The system of claim 30, wherein the preset time corresponds to the elapsed time between a triggering event and the beginning of a more vulnerable portion of the cardiac rhythm.

33. A method of performing percutaneous myocardial revascularization on the heart of a patient, comprising the steps of:

providing a first electrode disposed proximate the heart and a second electrode coupled to the body of the patient;

sensing a physiologically induced signal between the first electrode and the second electrode, the physiologically induced signal indicative of the cardiac rhythm of the patient;

detecting a less vulnerable portion of the cardiac rhythm of the heart; and ablating tissue proximate the first electrode when the less vulnerable portion of the cardiac rhythm is detected.

34. The method of claim 33, wherein the less vulnerable portion of the cardiac rhythm corresponds to a contracting portion of the cardiac rhythm.

35. The method of claim 33, wherein the less vulnerable portion of the cardiac rhythm corresponds to an R-wave portion of the cardiac rhythm.

36. The method of claim 33, wherein the first electrode is disposed proximate the distal end of a catheter.

37. The method of claim 36, further including the steps of inserting the catheter into a vascular system of the patient, and advancing the catheter within the vascular system of the patient until the first electrode is disposed proximate a wall of the heart.

38. A system for performing percutaneous myocardial revascularization of a patient's heart muscle, comprising:

a first electrode that delivers an ablation current to the patient's heart muscle;

a second electrode that collects the ablation current from the first electrode;

an ablation current source that selectively delivers an ablation current to the first electrode;

a sensing mechanism that senses a physiological signal induced between the first and second electrodes; and an ablation controller that times a predetermined interval when the physiological signal crosses a threshold, wherein the ablation controller enables the ablation current source to deliver the ablation current during the predetermined interval.

39. The system of claim 38, wherein the threshold is a voltage occurring between the first and second electrodes when the first electrode is in contact with a heart wall and the heart muscle is in a ventricular contraction of the cardiac rhythm.

40. The system of claim 38, wherein the predetermined interval begins upon detection that the heart is in a ventricular contraction of the cardiac rhythm and ends prior to the beginning of a T-wave of the heart's cardiac rhythm.

41. The system of claim 38, wherein the ablation controller includes a logic AND circuit that enables the ablation current source to deliver an ablation current at a time that is within the predetermined interval and if a user switch is activated.

* * * * *

UNITED STATES PATENT AND TRADEMARK OFFICE
CERTIFICATE OF CORRECTION

PATENT NO. : 6,666,863 B2
DATED : December 23, 2003
INVENTOR(S) : D.E. Wentzel et al.

It is certified that error appears in the above-identified patent and that said Letters Patent is hereby corrected as shown below:

<u>Column 9,</u>
Line 33, "claim 2," should read -- claim 8, --

Signed and Sealed this

Seventeenth Day of August, 2004

JON W. DUDAS
*Acting Director of the United States Patent and Trademark Office*